(12) United States Patent
Stork et al.

(10) Patent No.: US 7,491,944 B1
(45) Date of Patent: Feb. 17, 2009

(54) METHOD TO ANALYZE REMOTELY SENSED SPECTRAL DATA

(75) Inventors: Christopher L. Stork, Albuquerque, NM (US); Mark H. Van Benthem, Middletown, DE (US)

(73) Assignee: Sandia Corporation, Albuquerque, NM (US)

( * ) Notice: Subject to any disclaimer, the term of this patent is extended or adjusted under 35 U.S.C. 154(b) by 321 days.

(21) Appl. No.: 11/410,445

(22) Filed: Apr. 25, 2006

Related U.S. Application Data

(60) Provisional application No. 60/699,273, filed on Jul. 14, 2005.

(51) Int. Cl.
G06F 7/52 (2006.01)

(52) U.S. Cl. ............................................. 250/390.07
(58) Field of Classification Search ............ 250/390.07; 702/28; 382/276
See application file for complete search history.

(56) References Cited

U.S. PATENT DOCUMENTS

| | | | | |
|---|---|---|---|---|
| 6,584,413 | B1 * | 6/2003 | Keenan et al. | 702/28 |
| 6,675,106 | B1 * | 1/2004 | Keenan et al. | 702/28 |
| 7,283,684 | B1 * | 10/2007 | Keenan | 382/276 |

OTHER PUBLICATIONS

Tauler et al., Multivariate Curve Resolution Applied to Spectral Data from Multiple Runs of an Industrial Process, 1993, Anal. Chem., 65,2040.*

Keenan et al., Accounting for Poisson noise in the multivariate analysis of Tof-SIMS spectrum images, 2004, Surf. Interface Anal.,36,203-212.*

Chris L. Stork et al, "Multivariate curve resolution for the analysis of remotely sensed thermal infrared hyperspectral images", Proceedings of SPIE vol. 5546 (2004), pp. 271-284.

Nirmal Keshava and John F. Mustard, "Spectral Unmixing", IEEE Signal Processing Magazine, Jan. 2002 pp. 44-57.

S. J. Young, "Detection and Quantification of Gases in Industrial-Stack Plumes Using Thermal-Infrared Hyperspectral Imaging," the Aerospace Corporation, Aerospace Report No. ATR-2002(8407)-1, Feb. 10, 2002.

Christopher C. Funk et al, "Clustering to Improve Matched Filter Detection of Weak Gas Plumes in Hyperspectral Thermal Imagery," IEEE Transactions on Geoscience and Remote Sensing, vol. 39, No. 7, Jul. 2001 pp. 1410-1420.

Roma Tauler and Bruce Kowalski, "Multivariate Curve Resolution Applied to Spectral Data from Multiple Runs of an Industrial Process", American Chemical Society, vol. 65, No. 15, (1993) pp. 2040-2047.

(Continued)

*Primary Examiner*—David P Porta
*Assistant Examiner*—Djura Malevic
(74) *Attorney, Agent, or Firm*—Kevin W. Bieg

(57) ABSTRACT

A fast and rigorous multivariate curve resolution (MCR) algorithm is applied to remotely sensed spectral data. The algorithm is applicable in the solar-reflective spectral region, comprising the visible to the shortwave infrared (ranging from approximately 0.4 to 2.5 µm), midwave infrared, and thermal emission spectral region, comprising the thermal infrared (ranging from approximately 8 to 15 µm). For example, employing minimal a priori knowledge, notably non-negativity constraints on the extracted endmember profiles and a constant abundance constraint for the atmospheric upwelling component, MCR can be used to successfully compensate thermal infrared hyperspectral images for atmospheric upwelling and, thereby, transmittance effects. Further, MCR can accurately estimate the relative spectral absorption coefficients and thermal contrast distribution of a gas plume component near the minimum detectable quantity.

12 Claims, 11 Drawing Sheets

OTHER PUBLICATIONS

Rasmus Bro and Sijmen De Jongl, "A Fast Non-Negativity-Constrained Least Squares Algorithm," Journal of Chemometrics, vol. 11, 393-401 (1997).

Mark H. Van Benthem et al, "Application of equality constraints on variables during alternating least squares procedures," Journal of Chemometrics, 2002, vol. 16 pp. 613-622.

Michael R. Keenan, "Methods for Spectral Image Analysis by Exploiting Spatial Simplicity," U.S. Appl. No. 11/233,223, filed Sep. 22, 2005.

Henry F. Kaiser, "The Varimax Criterion for Analytic Rotation in Factor Analysis," Psychometrika, vol. 23 No. 3, Sep. 1958 pp. 187-200.

S. W. Sharpe, et al, Creation of 0.10 $cm^{-1}$ Resolution, Quantitative, Infrared Spectral Libraries for Gas Samples, Proceedings of SPIE vol. 4577 (2002) pp. 12-24.

Degui Gu et al, "Autonomous Atmospheric Compensation (AAC) of High Resolution Hyperspectral Thermal Infrared Remote-Sensing Imagery", IEEE Transactions on Geoscience and Remote Sensing, vol. 38, No. 6, Nov. 2000, pp. 2557-2570.

* cited by examiner

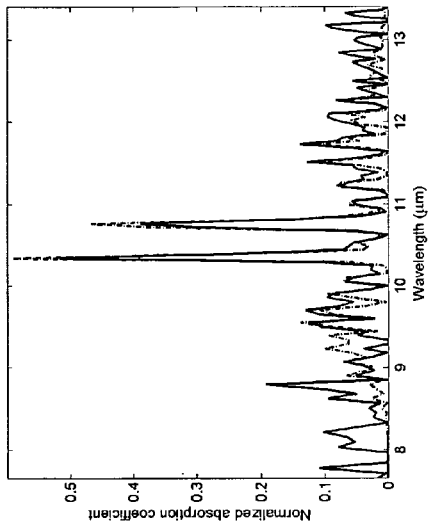
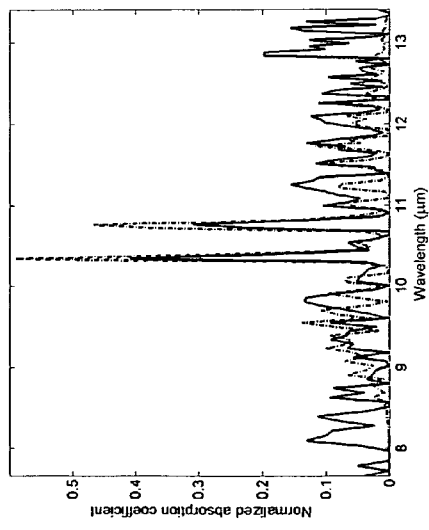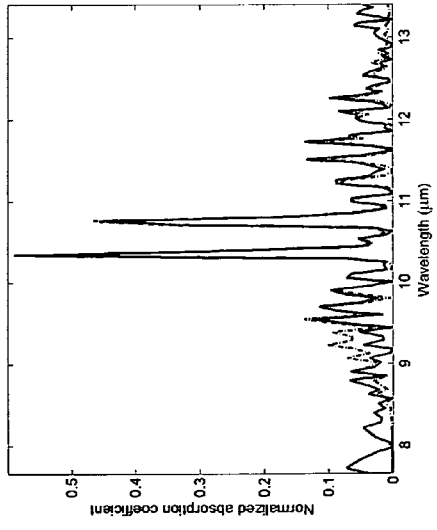

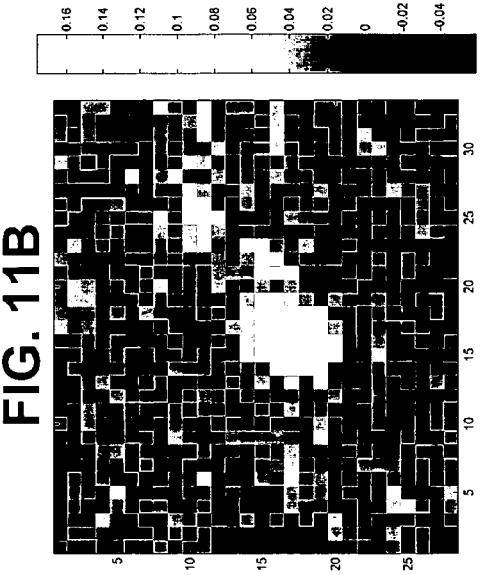
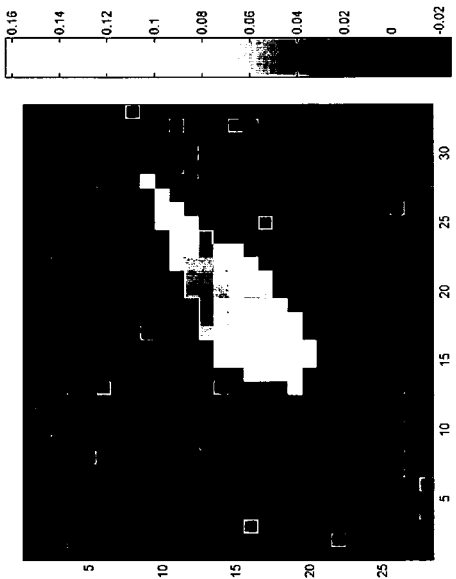
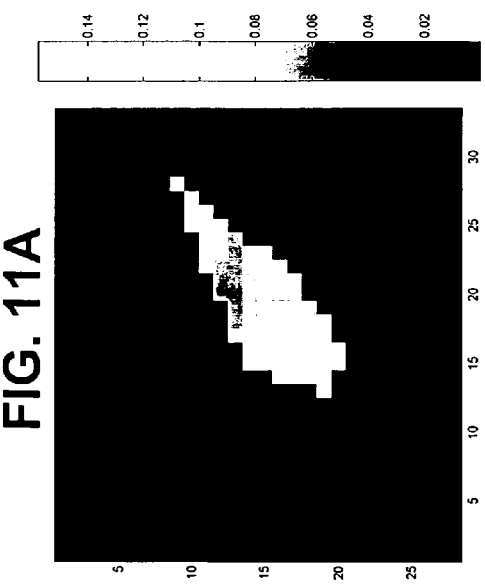
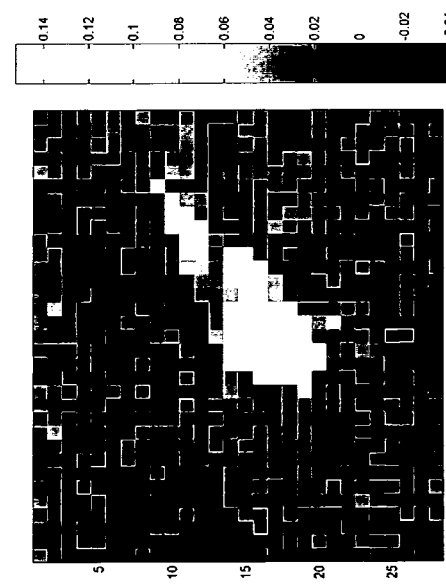

METHOD TO ANALYZE REMOTELY SENSED SPECTRAL DATA

CROSS-REFERENCE TO RELATED APPLICATION

This application claims the benefit of U.S. Provisional Application No. 60/699,273, filed Jul. 14, 2005, which is incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to remotely sensed spectral data processing and, in particular, to a method to analyze remotely sensed spectral data using multivariate curve resolution.

BACKGROUND OF THE INVENTION

Satellite and aircraft remote sensing systems have been increasingly used to aid weather prediction, agricultural forecasting, resource exploration, land cover mapping, environmental monitoring, industrial plant monitoring, civil defense, and military surveillance. Hyperspectral imaging systems promise enhanced scene characterization relative to univariate and multispectral technologies for these applications. Using a hyperspectral imaging system, data can be acquired across 100 or more spectral channels, offering superior spectral resolution. However, despite the inherent theoretical advantages of hyperspectral imaging in remote sensing applications, it has proven difficult to extract all of the useful information from these systems because of the overwhelming volume of data generated, confounding atmospheric effects, and the limited a priori knowledge regarding the scene. To address the challenges involved in the analysis of remotely sensed hyperspectral image data, spectral unmixing algorithms have been developed to deconvolve the endmembers and corresponding abundances of components contained within a given image data set. The term endmember refers to the spectral signature of a given pure component. See N. Keshava and J. F. Mustard, "Spectral Unmixing," *IEEE Signal Processing Magazine* 19(1), 44 (2002).

One can decompose the traditional spectral unmixing problem into a sequence of two consecutive steps: (1) endmember determination—estimate the set of unique endmembers for the components that comprise the mixed pixels in the scene, and (2) inversion—estimate the relative abundances of the components for each mixed pixel. Endmember determination is typically achieved through the use of laboratory-based library spectra, or the identification of pure pixels in the scene employing a method such as the pixel purity index. See S. J. Young, "Detection and Quantification of Gases in Industrial-Stack Plumes Using Thermal-Infrared Hyperspectral Imaging," *Aerospace Report No. ATR*-2002(8407)-1, pp. 1-19, The Aerospace Corporation, El Segundo, Calif., (2002); C. C. Funk et al., "Clustering to Improve Matched Filter Detection of Weak Gas Plumes in Hyperspectral Thermal Imagery," *IEEE Transactions on Geoscience and Remote Sensing* 39(7), 1410 (2001); and J. W. Boardman et al., "Mapping target signatures via partial unmixing of AVIRIS data," *Summaries, 5th JPL Airborne Earth Science Workshop*, JPL Publication 95-1, 23 (1995). Spectral libraries can be used to decompose individual pixels into their components based on a knowledge and comparison with the spectral characteristics of known target endmembers. However, spectral libraries are limited in that laboratory spectra are not representative of remotely acquired spectra because of differences in instrumentation and acquisition conditions. The use of spectral libraries also assumes an a priori model for the hyperspectral data and this approach fails when the pure spectrum for a component of interest is not contained within the library. While pure pixel-based approaches can be used to estimate endmembers directly from the scene, such approaches are typically time and computation intensive. Furthermore, it may be difficult or impossible to identify pure pixels in remote scenes with limited spatial resolution.

Therefore, a need remains for a method to perform rapid and comprehensive data exploitation of remotely sensed spectral data with limited a priori knowledge regarding the scene. According to the present invention, a fast and rigorous multivariate curve resolution (MCR) algorithm can be used to analyze remotely sensed spectral data. MCR is an algorithmic approach that focuses on recovering the endmember and abundance profiles of the components in an unresolved mixture when little or no prior information is available about the nature and composition of these mixtures.

SUMMARY OF THE INVENTION

The present invention is directed to a method to analyze remotely sensed spectral data, comprising acquiring an m sample by n channel remotely sensed spectral data set, X, which contains signal contributions from spectrally active materials, or components, on the surface and the intervening atmosphere; modeling the data set according to $X = C_{true} S_{true} T + 1 a^T + E_{instr}$, where $C_{true}$ is an m by p matrix of true abundances for the p components contained within a remote scene, $S_{true}$ is a corresponding p by n matrix of true spectral endmembers for the p components, T is a matrix of atmospheric transmittance values, 1 is a vector of ones, $a^T$ is a vector representing an additive, atmospheric component, and $E_{instr}$ is an m by n matrix describing instrument noise; calculating the atmospheric transmittance matrix T and additive atmospheric component $a^T$ to provide an atmospherically compensated data set according to $X_c = (X - 1a^T)T^{-1} = C_{true} S_{true} + E_{instr}$; and obtaining an MCR estimate of $C_{true}$ and $S_{true}$, subject to constraints. The remotely sensed spectral data set X can comprise solar-reflective spectral data or thermal emission spectral data. Principal Components Analysis (PCA) can be used to factor the atmospherically compensated data set $X_c$, the PCA factors can be rotated to provide a rotated abundance matrix $\tilde{C}$ and a rotated endmember matrix $\tilde{S}$, and MCR can be performed on the rotated abundance and endmember matrices. The PCA factorization can comprise non-linear iterative partial least squares, eigenanalysis, or singular value decomposition. The rotation of the PCA factors can comprise Quartimax or Varimax rotation.

For example, the method can be applied to a remotely sensed thermal infrared (TIR) data set, X. The remotely sensed TIR data set can be modeled according to $$X = GKT + BFT + 1I_u^T + E_{instr} = [\,G \;\; B \;\; 1\,] \begin{bmatrix} KT \\ FT \\ I_u^T \end{bmatrix} + E_{instr},$$

where G is an m by J matrix of thermal contrast coefficients for the J plume gases, K is a J by n matrix of spectral absorption coefficients for the J plume gases, B is an m by L matrix of amplitude coefficients for the L solids, F is an L by n matrix of spectral coefficients for the L solids, T is an n by n diagonal matrix with the n atmospheric transmittance values arranged along the diagonal, 1 is an m by 1 vector of ones, and $I_u^T$ is a 1 by n vector containing the n atmospheric upwelling terms, and $E_{instr}$ is an m by n matrix describing instrument noise. A multivariate curve resolution (MCR) estimate of the atmospheric upwelling, $I_u^T$, can be obtained, subject to constraints; the atmospheric transmittance matrix, T, can be calculated to provide an atmospherically compensated data set according to $$X_c = (X - 1I_u^T)T^{-1} =$$
$$GK + BF + E_{instr} = [\,G \;\; B\,] \begin{bmatrix} K \\ F \end{bmatrix} + E_{instr} = C_{true}S_{true} + E_{instr};$$

and an MCR estimate of G, K, B, and F can be obtained, subject to constraints. The atmospheric transmittance, T, can be calculated according to $\bar{\epsilon}_s(\lambda)\tau(\lambda) = (\bar{x}(\lambda) - I_u(\lambda))/B_s(\lambda,T)$, where $\bar{\epsilon}_s(\lambda)$ is the mean surface emissivity over all the pixels at wavelength $\lambda$, $\bar{T}$ is the mean surface temperature over all the pixels, $B_s(\lambda,\bar{T})$ is the Planck blackbody radiance function evaluated at wavelength $\lambda$ and the mean surface temperature $\bar{T}$, $\tau(\lambda)$ is the atmospheric transmittance at wavelength $\lambda$, and $I_u(\lambda)$ is the upwelling atmospheric radiance at wavelength $\lambda$.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIGS. 10A-C show MCR-estimated, normalized spectral absorption coefficients (-) and true resampled, normalized spectral absorption coefficients (-.) for ammonia at column densities of 2.5 ppmm (FIG. 10A), 5 ppmm (FIG. 10B), and 10 ppmm (FIG. 10C).

FIG. 11A shows true normalized thermal contrast image for ammonia plumes. FIGS. 11B-D show MCR-estimated, normalized thermal contrast images at ammonia column densities of 2.5 ppmm (FIG. 11B), 5 ppmm (FIG. 11C), and 10 ppmm (FIG. 11D).

DETAILED DESCRIPTION OF THE INVENTION

Figure 1:
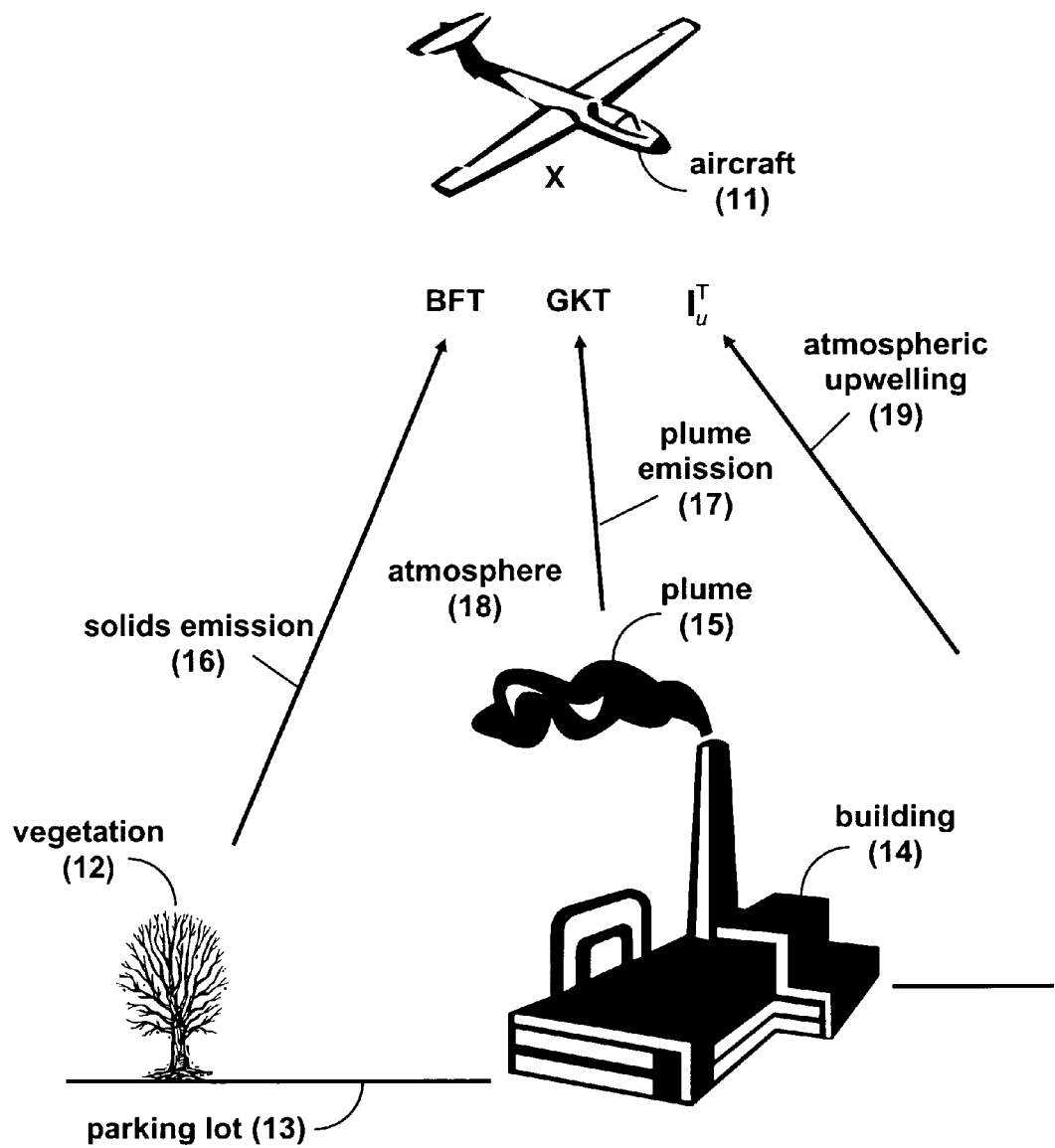
FIG. 1 shows a schematic illustration of the acquisition of remote thermal infrared (TIR) hyperspectral image data using a sensor aboard an aircraft.

MCR differs from traditional spectral unmixing algorithms in that it performs endmember determination and abundance estimation iteratively. Starting with an initial guess for either the endmembers or abundances, MCR alternately estimates the endmembers and abundances. Because of the iterative nature of MCR, a complete knowledge of the endmembers and abundances is not required. MCR is very flexible in that it can incorporate varying amounts of information regarding the data set, ranging from the use of random numbers as initial guesses for the endmembers and abundances, to knowledge of the endmembers and abundances of one or more components. MCR iteratively refines the initial guesses for the endmembers and abundances such that they minimize a least squares criterion and satisfy any imposed constraints such as non-negativity or equality of the proposed solutions. See R. Tauler et al., "Multivariate Curve Resolution Applied to Spectral Data from Multiple Runs of an Industrial Process," *Analytical Chemistry* 65, 2040 (1993).

MCR has distinct advantages relative to both spectral library and pure pixel based approaches for spectral unmixing. MCR is more broadly applicable than spectral library based unmixing methods in that one can identify and quantify components that are not contained within a spectral library. In the event that an endmember extracted by MCR is not contained in a spectral library, an expert spectroscopist can identify the endmember by interpreting its spectral features. A disadvantage of pure pixel based methods for endmember determination is that endmembers are derived using only a small number of pixels within the remote scene, making them sensitive to outliers. Using MCR, endmembers are estimated using information contained in all pixels in the scene.

General MCR Model

The following conventions are used in the presentation of the MCR model equations. Scalars are represented by italics. Column vectors are denoted by boldface lowercase letters. Row vectors are represented as transposed column vectors, with transposition symbolized by the superscript T, e.g., $\mathbf{x}^T$. All matrices are represented by boldface uppercase letters. The inverse of a matrix is represented by a superscripted '-1', e.g., $\mathbf{X}^{-1}$.

MCR operates under two key assumptions: (1) a linear model is appropriate for the given data set, and (2) the number of pure components within the data set in question is known or can be reasonably estimated. An m by n linear data set, X, can be decomposed as the product of two pure component matrices and a residual matrix $$X = CS + E \qquad (1)$$

where C is the m by p matrix of abundances, S is the p by n matrix of spectral endmembers, E is the m by n matrix of residuals describing unmodeled variation, m corresponds to the number of samples in the data set, n corresponds to the number of spectral channels, and p is the number of pure components. MCR is implemented using an alternating least squares approach. Given the number of components within the data set, MCR is initialized by selecting a starting guess for either C or S. Assuming that an initial guess is generated for S, each row, or endmember, of S is then normalized to unit length. Given this initial guess for S, C is estimated using least squares:

$$\hat{C} = \min(C) \|X - CS\|_F \qquad (2)$$

subject to constraints on C. Setting $C = \hat{C}$ as the current best estimate for the abundances, the estimate for S is updated as $$\hat{S} = \min(S) \|X - CS\|_F \qquad (3)$$

subject to constraints on S. $\hat{S}$ is now the current best estimate for the endmembers, such that $S = \hat{S}$. The steps outlined in equations (2) and (3) iterate until convergence. Alternatively, the roles of C and S can be easily interchanged by making an initial guess for C and first solving equation (3) for S.

In the absence of any constraints, there are an infinite number of solutions to this linear decomposition. In the analysis of the data sets herein, two constraints were applied to narrow the solution space to those that are physically acceptable: (1) non-negativity of endmembers (endmembers are constrained to be positive or zero), and (2) an equality constraint on the known relative abundances of one component in the data set (the relative abundances are constrained to equal the known values). Fast and rigorous non-negativity constraints were imposed using a modified version of Bro's algorithm. See R. Bro and S. De Jong, "A fast non-negativity-constrained least squares algorithm," *Journal of Chemometrics* 11, 393 (1997). Likewise, equality constraints were imposed using an efficient and rigorous implementation of Lawson and Hanson's method. See C. L. Lawson and R. J. Hanson, *Solving Least Squares Problems*, Prentice-Hall, Englewood Cliffs, N.J. (1974); and M. H. Van Benthem et al., "Application of equality constraints on variables during alternating least squares procedures," *Journal of Chemometrics* 16, 613 (2002).

Linear Mixing Model for a Scene

An analytical model describing the mixing of different materials, or components, in an outdoor scene provides the necessary foundation for the development of algorithms to estimate the endmembers, or pure component spectra, and corresponding abundances of these components in mixed pixels. The underlying premise of mixture modeling is that within a given outdoor scene, the surface can be represented by a finite number of unique materials, or components, that have constant spectral properties across the scene. The pure spectra of these unique components (e.g., water, minerals, vegetation) are referred to as endmembers, while the proportions in which the components occur in a mixed pixel are referred to as abundances. According to the linear mixing model, spectra measured by an imaging or non-imaging spectrometer positioned at the surface can be represented by the following equation:

$$X_{surface} = C_{true} S_{true} + E_{instr} \qquad (4)$$

where $C_{true}$ is an m by p matrix of true abundances, $S_{true}$ is a p by n matrix of true spectral endmembers, $E_{instr}$ is an m by n matrix describing instrumental noise, m corresponds to the number of measured sample locations, n corresponds to the number of spectral channels, and p is the number of unique, spectrally active components occurring within the scene. Equation (4) is applicable both in the solar-reflective spectral region, comprising the visible to the shortwave infrared (ranging from approximately 0.4 to 2.5 µm), and in the thermal emission spectral region, comprising the thermal infrared (ranging from approximately 8 to 15 µm). In the solar-reflective spectral region, the source of energy is the sun, while in the thermal emission spectral region detected radiation is emitted by objects on the surface.

Remotely positioning the spectrometer above the surface (e.g., on an airplane or a satellite) will result in additional at-sensor signal complexity due to intervening atmospheric contributions to the measured signal. Remotely acquired spectra can be reduced to the at-surface spectra, represented by equation (4), through the application of an appropriate atmospheric compensation algorithm. For example, the remotely sensed spectral data can be modeled according to:

$$X = C_{true} S_{true} T + 1 a^T + E_{instr} \qquad (5)$$

where T is an n by n matrix of atmospheric transmission terms, 1 is an m by 1 vector of ones, and $a^T$ is a 1 by n vector representing an additive, atmospheric component. The atmospheric contributors to the signal, T and $a^T$, can then be estimated and removed using an atmospheric compensation algorithm, such as MCR, to provide an atmospherically compensated data set, $X_c = (X - 1a^T)T^{-1} = C_{true} S_{true} + E_{instr}$. MCR estimates of $C_{true}$ and $S_{true}$ can then be obtained, subject to constraints.

Equation (4) is very similar to equation (1), with the exception that equation (4) contains the true component abundances and endmembers, as opposed to MCR-estimated abundances and endmembers. Accordingly, both in the solar-reflectance spectral region and in the thermal emission spectral region, MCR can be applied to measured, at-surface spectra, or atmospherically compensated, remotely acquired spectra in order to estimate the abundances and endmembers for surface components occurring within the data set. While the examples presented herein are applied to the analysis of thermal infrared hyperspectral image data, the invention can similarly be applied to spectra acquired using non-imaging spectrometers, to multispectral data sets (defined as data containing 2 to 99 spectral channels), and to solar-reflectance and midwave infrared spectral data.

Method to Analyze Remotely Sensed TIR Hyperspectral Image Data Using MCR

As an example of MCR's utility in the analysis of remotely sensed spectral data, the method of the present invention was applied to the standoff detection of a chemical gas plume. Standoff detection of such gas plumes has become important, especially for industrial plant monitoring and civil defense applications. Passive analysis of such plumes relies on the imbalance of emission and absorption in the thermal infrared (TIR) of the electromagnetic spectrum. If the gas plume is warmer than the temperature of the background, the spectral bands of the gas molecules appear as an emission, and the same bands appear as an absorption, if the gas is colder than the background. Therefore, hyperspectral imaging in the TIR enables remote sensing of both the spatial distribution of gas plumes and the identification and quantification of trace gas components within the plumes.

Employing minimal a priori knowledge, notably non-negativity constraints on the extracted endmembers and a constant abundance constraint for the atmospheric upwelling component, MCR can successfully compensate TIR hyperspectral images for both atmospheric upwelling and transmittance effects on the spectral data. In the example described herein, a semi-synthetic approach is used to obtain image data containing a gas plume by adding emission gas signals onto real hyperspectral image data. In this manner, the true gas plume endmember and abundances are known, and the ability of MCR to isolate the endmember profile of the gas plume component (plume identification) and provide estimates of the relative abundances of this component (plume quantification) can be readily evaluated.

As an example of the present invention, in FIG. 1 is shown a schematic illustration of the acquisition of remote TIR hyperspectral image data of a ground scene using a sensor aboard a remote aircraft 11. The scene can comprise background solids (e.g., vegetation 12, a parking lot 13, a building 14), and a gas plume 15 released from a stack on the building 14. The emission 16 and 17 from the solids and plume will be attenuated by transmission through the atmosphere 18 between the ground and the aircraft 11. In addition to the emissions 16 and 17 from the solids and plume, the sensor will also detect emission 19 from the atmosphere, referred to as atmospheric upwelling.

Figure 2:
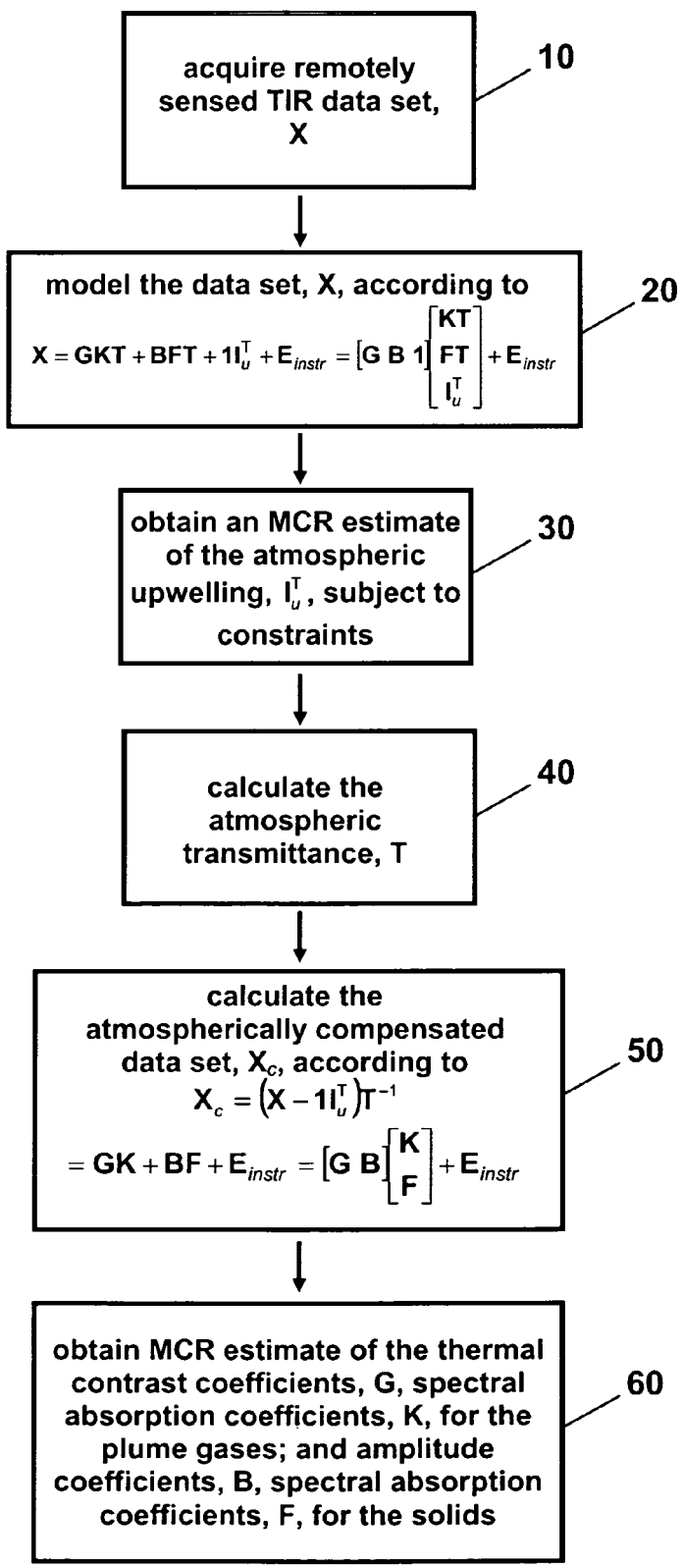
FIG. 2 shows a method to analyze a remotely sensed TIR data set using MCR.

In FIG. 2 is shown a method to analyze the remotely sensed TIR hyperspectral image data using MCR. At step 10, remotely sensed TIR images are acquired that can be represented by a data set, X. At step 20, the data set, X, comprising m samples and n spectral channels and containing solid and gas plume components can be modeled as:

$$X = GKT + BFT + 1I_u^T + E_{instr} = [G \; B \; 1]\begin{bmatrix} KT \\ FT \\ I_u^T \end{bmatrix} + E_{instr} \quad (6)$$

where G is an m by J matrix of thermal contrast coefficients for the J plume gases, K is a J by n matrix of spectral absorption coefficients for the J plume gases, B is an m by L matrix of amplitude coefficients for the L solids, F is an L by n matrix of spectral coefficients for the L solids, T is an n by n diagonal matrix with the n atmospheric transmittance values arranged along the diagonal, 1 is an m by 1 vector of ones, $I_u^T$ is a 1 by n vector containing the n atmospheric upwelling terms and $E_{instr}$ is an m by n matrix describing instrumental noise. See S. J. Young. Equation (6) takes the same form as equation (1), where the G and B matrices and the vector 1 are analogous to the abundance matrix, C, and the KT and FT product matrices and the vector $I_u^T$ are analogous to the endmember matrix, S.

In inspecting equation (6), it is apparent that MCR can directly estimate the atmospheric upwelling, $I_u^T$, since it is a linear, additive term. Therefore, at step 30, a scaled, MCR-based estimate of the atmospheric upwelling is obtained by imposing a constant abundance constraint on the upwelling component, represented in equation (6) by the vector, 1 (i.e., this is equivalent to requiring a homogeneous atmosphere).

Given the MCR estimate of the atmospheric upwelling, $I_u^T$, the atmospheric transmittance, T, can be calculated at step 40, thereby providing a means of compensating at-sensor TIR spectra. The mean at-sensor spectral radiance at wavelength λ over all the pixels in the data set can be approximated as:

$$\bar{x}(\lambda) \cong \bar{\epsilon}_s(\lambda)B_s(\lambda,\bar{T})\tau(\lambda)+I_u(\lambda) \quad (7)$$

where $\bar{\epsilon}_s(\lambda)$ is the mean surface emissivity over all the pixels at wavelength λ, $\bar{T}$ is the mean surface temperature over all the pixels, $B_s(\lambda, \bar{T})$ is the Planck blackbody radiance function evaluated at wavelength λ and the mean surface temperature $\bar{T}$, $\tau(\lambda)$ is the atmospheric transmittance at wavelength λ, and $I_u(\lambda)$ is the atmospheric upwelling radiance at wavelength λ. See S. J. Young.

Rearranging equation (7), an estimate of the atmospheric transmittance at wavelength λ is obtained as follows:

$$\bar{\epsilon}_s(\lambda)\tau(\lambda) = (\bar{x}(\lambda) - I_u(\lambda))/B_s(\lambda,\bar{T}). \quad (8)$$

This estimate is dependent on the knowledge of the mean surface temperature, $\bar{T}$. An estimate of the surface temperature can be obtained by calculating the brightness temperature, $T_B(\lambda)$, at each wavelength as $$T_B(\lambda) = \frac{c_2}{\lambda \ln\left[1 + \frac{c_1}{\lambda^5 \bar{x}(\lambda)}\right]} \quad (9)$$

where $c_1 = 1.191 \times 10^{10}$ µf-µm$^5$ and $c_2 = 14388$ µm-K. The maximum brightness temperature as a function of wavelength can be used as an estimate of the mean surface temperature, $\bar{T}$. This maximum brightness temperature corresponds to the wavelength where there is the highest atmospheric transmittance and the at-sensor radiance is least affected by the atmosphere.

In addition to being dependent on the accuracy of the mean surface temperature, the quality of the MCR-based estimate of the atmospheric transmittance in equation (8) is also dependent on the mean surface emissivity, $\bar{\epsilon}_s(\lambda)$. The estimate in equation (8) becomes more accurate as the mean surface emissivity approaches unity. The emissivities for objects in remote scenes typically range between 0.9 and 1, and, with few exceptions, equation (8) provides a reasonable estimate of the atmospheric transmittance.

The radiance data can then be compensated for emission and absorption effects of the atmosphere at step 50. Given the MCR-based estimates of the atmospheric upwelling radiance, $I_u(\lambda)$, and transmittance, $\tau(\lambda)$, the surface radiance at the i$^{th}$ pixel, $x_c(\lambda, i)$, can be calculated as $$x_c(\lambda,i) = (x(\lambda,i) - I_u(\lambda))/\tau(\lambda) \quad (10)$$

Therefore, the atmospherically compensated TIR data set, $X_c$, can be calculated as:

$$X_c = (X - 1I_u^T)T^{-1}. \quad (11)$$

$X_c$ is an approximation of the spectra that would have been acquired in the absence of atmospheric effects. The atmospherically compensated TIR data set, $X_c$, can be modeled as:

$$X_c = GK + BF + E_{instr} = [G \; B]\begin{bmatrix} K \\ F \end{bmatrix} + E_{instr} \quad (12)$$

At step 60, an MCR estimate can be obtained for the thermal contrast coefficients, G, for the plume gases, the spectral absorption coefficients, K, for the plume gases, the amplitude coefficients, B, for solids, and the spectral coefficients, F, for solids, using the atmospherically compensated TIR data set.

A multi-step procedure can be used to obtain the MCR estimate at step 60. The multi-step procedure can comprise Principal Components Analysis (PCA) factorization of the data set, followed by rotation of the PCA factors, and finally MCR of the rotated factors. As is well known to those having skill in the art, there are many algorithms that can be used to perform the PCA factorization, including nonlinear iterative partial least squares, eigenanalysis, and singular value decomposition (SVD). In particular, SVD is a method that is often used to perform PCA. The constraints imposed by PCA are that the spectral and abundance factors must contain orthogonal components and that the components serially maximize the variance in the data that each accounts for. Unfortunately, neither constraint has any basis in physical reality; thus, the components obtained via PCA are abstract and not easily interpreted. Therefore, PCA may enable the detection of a plume, but not the identification of plume gases. Transformation or rotation of PCA factors can be used to obtain more readily interpretable factors. The matrix that is used to perform the rotation can be determined by one of the Orthomax-family of procedures (e.g., Quartimax or Varimax). Finally, MCR can be used to apply additional constraints to further refine the rotated factors. Typically, the refinement requires an iterative algorithm. For example, constraints can force spectra and abundances to be non-negative, yielding more physically realistic endmembers and abundances. Therefore, the three step analysis provides both the spatial distribution of the gas plume and the identification of trace gases within the plume. See U.S. patent application Ser. No. 11/233,223 to M. R. Keenan; and H. F. Kaiser, "The varimax criterion for analytic rotation in factor analysis," *Psychometrika* 23, 187 (1958).

Figure 3:
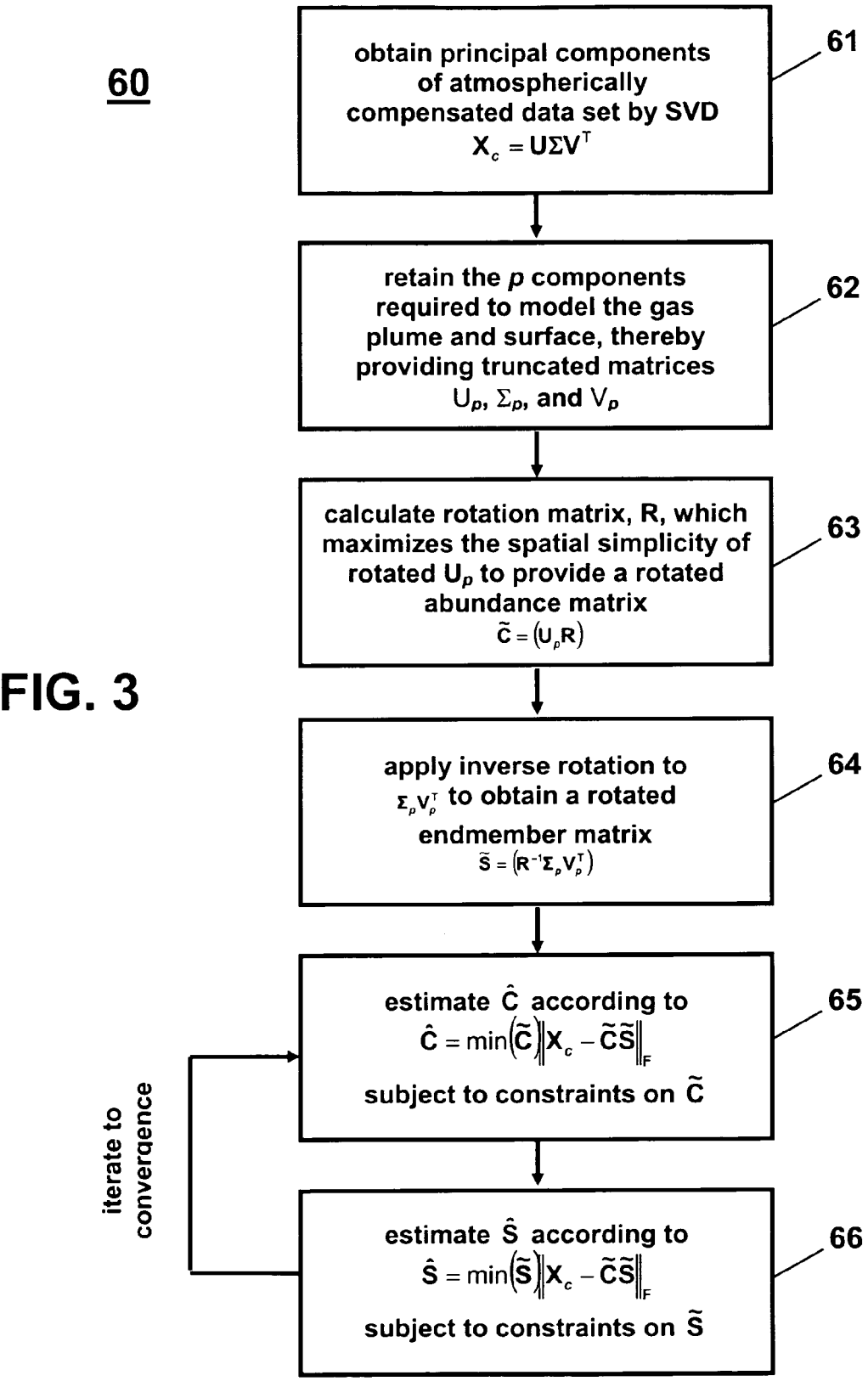
FIG. 3 shows a multi-step procedure for performing step 60 in FIG. 2.

The SVD, Varimax rotation, and MCR steps that can be used to perform step 60 are shown in FIG. 3.

At step 61, SVD is applied to the atmospherically compensated TIR data, $X_c$, and used to calculate the m by n left singular matrix, U, the n by n right singular matrix, V, and the n by n singular value matrix, $\Sigma$, which maximally describes the variance in the data set:

$$X_c = U \Sigma V^T \quad (13)$$

The left singular matrix, U, describes the image space, the right singular matrix, V, describes the spectral space, while the singular values, arranged along the diagonal of the singular value matrix, $\Sigma$, quantify the amount of variance described by each component.

SVD has the useful property that the space spanned by the first p columns of V represent, in a least squares sense, the best rank-p approximation to the space spanned by the rows of $X_c$. The remaining n-p columns of V represent experimental noise or error and can be discarded. Therefore, at step 62, the p most significant components are retained, thereby providing the truncated matrices $U_p$, $\Sigma_p$, and $V_p$. The number of retained components, p, can be determined by comparing images constructed from the left singular matrix, U, to the known spatial distribution of the plume. All the components required to model the surface and the gas plume are typically retained.

At step 63, Varimax rotation can be applied to the m by p left singular matrix, $U_p$, corresponding to the p retained columns of U. See M. R. Keenan. A p by p rotation matrix, R, can be calculated which maximizes the spatial simplicity of the rotated $U_p$ matrix. The rotation matrix is applied spatially to obtain an m by p abundance matrix, $\tilde{C} = (U_p R)$. Likewise, at step 64, the inverse rotation is applied to $\Sigma_p V_p^T$, where $\Sigma_p$ is the p by p diagonal matrix containing the retained singular values along the diagonal, and $V_p$ is the n by p right singular matrix, corresponding to the retained columns of V. The rotation matrix is applied spectrally to obtain a p by n endmember matrix, $\tilde{S} = (R^{-1} \Sigma_p V_p^T)$. Therefore, the atmospherically compensated TIR data can be represented by the rotated factors, according to $$X_c = (U_p R)(R^{-1} \Sigma_p V_p^T) + E = \tilde{C}\tilde{S} + E \quad (14)$$

Performing Varimax rotation in the spatial domain, as opposed to the spectral domain which is common practice, is an advantageous approach for processing remote sensing data, as the components within a remote scene are often spatially orthogonal (i.e., the image comprises spatially discrete component phases).

MCR can be applied to the rotated atmospherically compensated TIR data to improve the surface and gas plume endmember and component abundance estimates. At step 65, given this initial guess for $\tilde{S}$, $\hat{C}$ is estimated using least squares:

$$\hat{C} = \min(\tilde{C}) \| X_c - \tilde{C}\tilde{S} \|_F \quad (15)$$

subject to constraints on $\tilde{C}$. Setting $\tilde{C} = \hat{C}$ as the current best estimate for the abundances, the estimate for S is updated at step 66 as $$\hat{S} = \min(\tilde{S}) \| X_c - \tilde{C}\tilde{S} \|_F \quad (16)$$

subject to constraints on $\tilde{S}$. $\hat{S}$ is now the current best estimate for the endmembers, such that $\tilde{S} = \hat{S}$. Steps 65 and 66 are iterated until convergence. Alternatively, the roles of $\tilde{C}$ and $\tilde{S}$ can be easily interchanged by making an initial guess for $\tilde{C}$ and first solving step 66 for $\tilde{S}$.

MCR can be validly applied to atmospherically compensated TIR data because equation (12) takes the same form as equation (1), where the G and B matrices are analogous to the abundance matrix, C, i.e., CZ=[G B], and the K and F matrices are analogous to the endmember matrix, S, i.e., $$Z^{-1} S = \begin{bmatrix} K \\ F \end{bmatrix}.$$

Here, Z is a p by p diagonal matrix where the diagonal elements contain the scaling factors for the p components. These scaling factors are necessary, because the endmember estimates, S, obtained by MCR are relative and scaled to unit length. Assuming there is a single gas plume component in the scene, the endmembers for the (p −1) non-plume components can be initialized using the corresponding rows of the Varimax endmember matrix, while the endmember profile for the plume component can be initialized using randomly selected, uniformly distributed values ranging between zero and one. For the gas plume component, an equality constraint can be applied to the Varimax plume abundance estimate. An MCR non-negativity constraint can be applied in estimating the spectral absorption coefficients, K, for plume gases and spectral coefficients, F, for solids, as it is not plausible from a chemical or physical standpoint for these pure spectra to take on negative values. However, in order to accommodate both gas plume emission and absorption, the thermal contrast coefficients, G, for the plume gases can be allowed to take on both positive and negative values in MCR.

Application of MCR Model to Remotely Sensed TIR Data

The MCR model was applied to real hyperspectral TIR image data, acquired using the Spatially Enhanced Broadband Array Spectrograph System (SEBASS) TIR sensor. See B. R. Johnson, "Inscene atmospheric compensation, application to SEBASS data collected at the ARM site, part I," *Aerospace Report No. ATR*-99(8407)-1 Part I, pp. 1-29, The Aerospace Corporation, El Segundo, Calif. (1998). With this sensor, data collection is carried out by scanning the projection of the spectrograph entrance slit along the ground with the aircraft motion. The slit projection is perpendicular to the flight direction. The acquired data was used to evaluate the performance of MCR in terms of atmospheric compensation and gas plume identification and quantification. The SEBASS data set used in this evaluation was of dimensions 128 by 1000 by 128, corresponding to 128 pixels along a line perpendicular to the ground path, 1000 frames, and 128 spectral channels. The 128 spectral channels were acquired over a spectral range of 7.65 to 13.55 μm. The spectral resolution of the SEBASS sensor was about 0.05 μm. The SEBASS sensor was operated at an altitude of approximately 6000 feet above ground level. The ground spatial distance was approximately 2 m for each pixel. The unit of spectral radiance measured by the SEBASS sensor was μW/cm$^2$/sr/μm, denoted by the symbol μf.

All MCR analyses were performed on a 28 pixel by 33 pixel subregion of the full 128 pixel by 1000 pixel by 128 spectral channel SEBASS data set. The image subregion is shown as a black rectangular box in FIG. 4, with a synthetic plume 15 superposed on the SEBASS data set. Prior to performing MCR, spectral channels subject to significant instrumental artifacts were identified and removed from subsequent analyses. In all MCR analyses, channels 125 through 128, encompassing a spectral range from 13.44 to 13.55 μm, were removed.

In a first experiment, MCR was applied to the uncompensated TIR data, X, and used to estimate the atmospheric upwelling, $I_u^T$, and transmittance, T, according to steps 10-40 (i.e., equations (6)-(9)). A four-component MCR model was used, and 10000 iterations were performed. The number of components was set to four in order to model the four primary contributors to the uncompensated TIR data, notably vegetation 12, a parking lot 13, a building 14, and the atmospheric upwelling. A constant abundance constraint of one was imposed on the component modeling the atmospheric upwelling. A non-negativity constraint was applied to all the endmembers. All four endmembers were initialized using randomly selected, uniformly distributed values ranging between zero and one. The MCR-based estimates of the atmospheric upwelling and transmittance were used to compensate the TIR data, X, according to step 50 (i.e., equation (11)) and the atmospherically compensated TIR data, $X_c$, were used in all subsequent analyses.

The MCR-based upwelling and transmittance estimates were compared to those obtained using the Inscene Atmospheric Compensation (ISAC) algorithm. See B. R. Johnson. ISAC is a univariate atmospheric compensation algorithm which is dependent on the natural occurrence of blackbody objects, such as water or vegetation, within a scene to perform atmospheric compensation. This dependence on blackbody objects makes the correction of desert scenes problematic. ISAC utilizes only a small subset of pixels in deriving its atmospheric estimates, discarding information contained in the non-blackbody pixels. Because of the lack of detailed radiosonde measurements for the site in this study, the ISAC algorithm served as a de facto standard by which the MCR-based atmospheric compensation approach was evaluated. Since ISAC is a univariate method, individual atmospheric upwelling and transmittance estimates are derived for each spectral channel. Conversely, MCR is a multivariate technique that takes advantage of correlations between spectral channels. Therefore, ISAC requires a large number of pixels to perform reliable atmospheric compensation, whereas MCR can perform atmospheric compensation in local image regions utilizing a small number of pixels. In deriving atmospheric compensation estimates for the comparison, the ISAC algorithm was applied to the full 128 pixel by 1000 pixel image region, while MCR was applied to the defined 28 pixel by 33 pixel image subregion. ISAC was applied to the full image region, since there was an insufficient number of blackbody pixels in the image subregion for ISAC to achieve reliable atmospheric upwelling and transmittance estimates.

Figure 4:
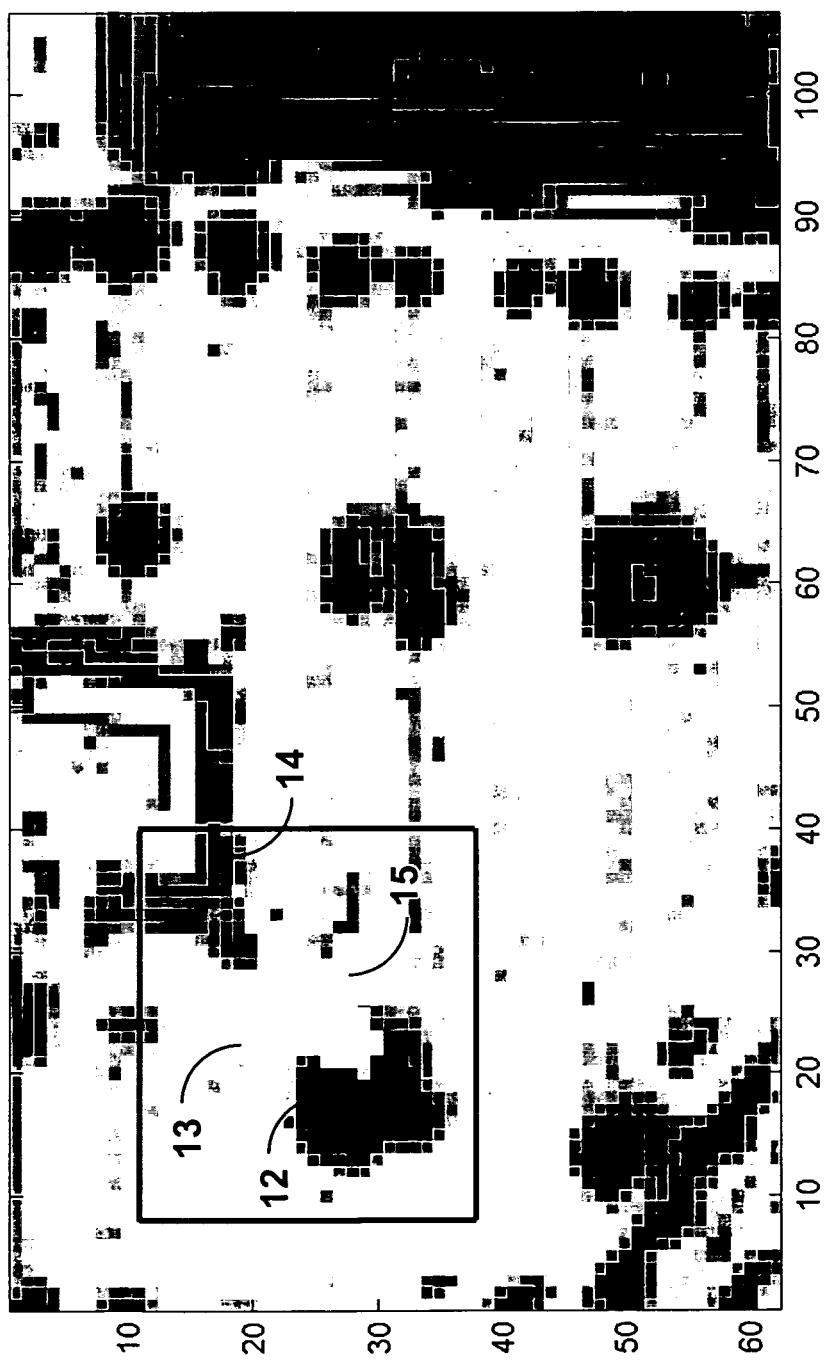
FIG. 4 shows a SEBASS TIR image. The image subregion analyzed using MCR is denoted by the black rectangular box. Pixels comprising the synthetic plume are denoted by the semi-transparent, white overlay.

Following MCR-based atmospheric compensation of the TIR data, synthetic gas plumes were added to the data. The spatial extent of each synthetic gas plume 15 is depicted in FIG. 4. Each synthetic gas plume was added to the atmospherically compensated TIR data, $X_c$, to provide a post-plume, atmospherically compensated data set, $X_{c,P}$, using the following model:

$$x_{c,P}(\lambda, i) = \sum_{j=1}^{J} G_j(i) k_j(\lambda) + x_{c,0}(\lambda, i) \quad (17)$$

$$= \sum_{j=1}^{J} g_{jP}(i)(B_P(\lambda_j, T_{P(i)}) - \varepsilon_S(\lambda_j, i) B_S(\lambda_j, T_{S(i)})) k_j(\lambda) + x_{c,0}(\lambda, i)$$

where P refers to the plume, S to the surface, $G_j(i)$ is the thermal contrast coefficient for the $j^{th}$ gas and $i^{th}$ pixel, $k_j(\lambda)$ is the spectral absorption coefficient for the $j^{th}$ gas at wavelength $\lambda$, $g_{jP}(i)$ is the plume contribution to the column density of the $j^{th}$ gas for the $i^{th}$ pixel in the sensor line of sight, $\lambda_j$ is the characteristic bandcenter of the $j^{th}$ gas, $T_{P(i)}$ is the plume temperature for the $i^{th}$ pixel, $T_{S(i)}$ is the surface temperature for the $i^{th}$ pixel, $x_{c,0}(\lambda,i)$ corresponds to the atmospherically compensated radiance for the $i^{th}$ pixel at wavelength $\lambda$ before the addition of the synthetic plume (pre-plume, atmospherically compensated radiance), and $x_{c,P}(\lambda,i)$ is the atmospherically compensated radiance for the $i^{th}$ pixel at wavelength $\lambda$ after the addition of the synthetic plume (post-plume, atmospherically compensated radiance). The term $\varepsilon_s(\lambda_j,i)B_s(\lambda_j, T_{s(i)})$ corresponds to the pre-plume, atmospherically compensated radiance for the $i^{th}$ pixel at the characteristic bandcenter for the $j^{th}$ plume gas. The term $B_P(\lambda_j,T_{P(i)})$ corresponds to the Plank blackbody radiance function evaluated at wavelength $\lambda_j$ and temperature $T_{p(i)}$. As a direct result of equation (17), if the plume temperature matches the underlying surface temperature, the thermal contrast is zero and the plume cannot be detected using TIR.

Synthetic plumes containing ammonia were added to the pre-plume, atmospherically compensated TIR data. High resolution spectral absorption coefficients for ammonia from Pacific Northwest National Laboratory were used to generate the synthetic plumes. See S. W. Sharpe et al., "Creation of 0.10 cm$^{-1}$ Resolution, Quantitative, Infrared Spectral Libraries for Gas Samples," *Proceedings of the SPIE, Vibrational*

Figure 5:
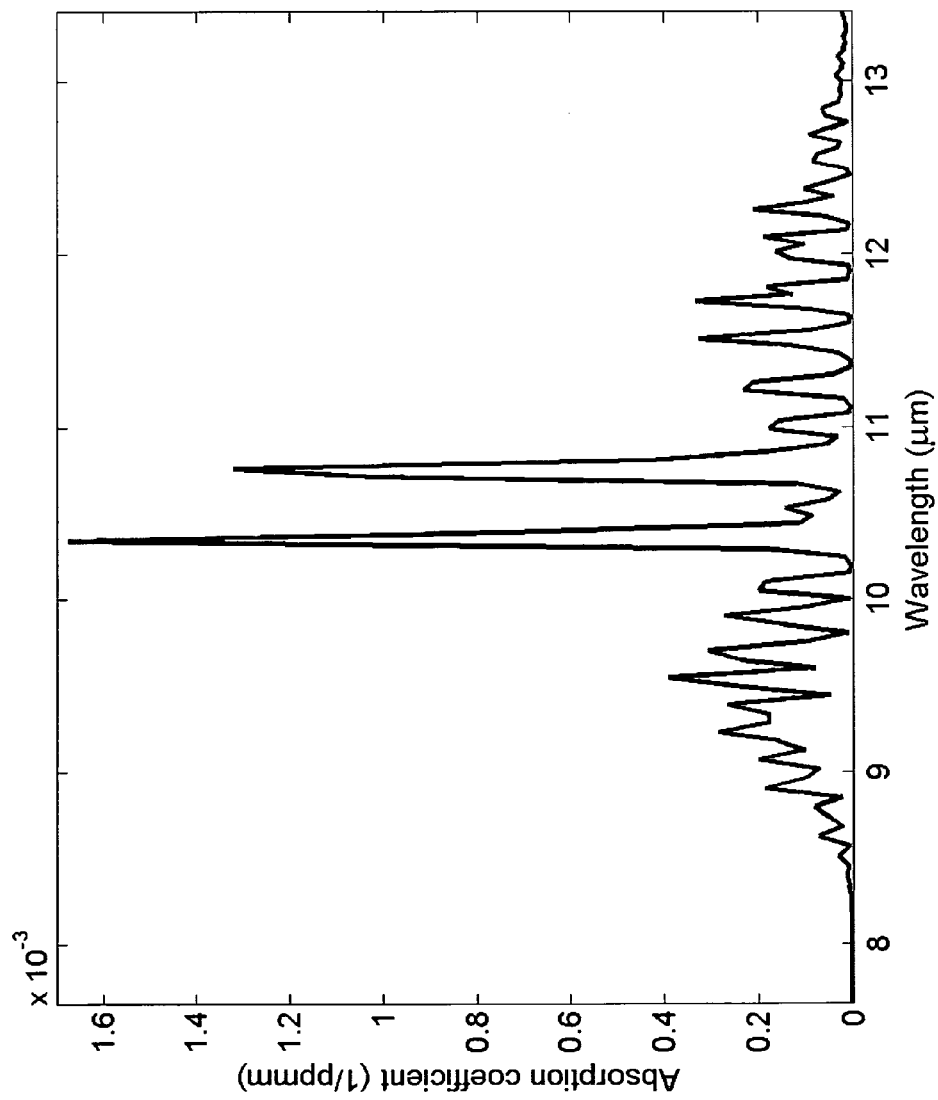
FIG. 5 shows the resampled spectral absorption coefficients for ammonia used in generating the synthetic plumes.

*Spectroscopy-Based Sensor Systems* 4577, 12 (2002). Spectral absorption coefficient data, measured in units of 1/parts-per-million-meter (1/ppmm), were provided at a spectral resolution of 0.12 cm$^{-1}$, a total sample pressure of 1 atm, and a temperature of 25° C. The spectral absorption coefficients for ammonia are independent of temperature between 15 and 80° C. See S. J. Young. The high resolution ammonia spectrum was resampled onto the SEBASS wavelength axis using a triangular slit function. The triangular slit function achieves a maximum at the center of a spectral channel and decreases to zero at the centers of the two adjacent channels. The resampled spectral absorption coefficients for ammonia are shown in FIG. 5. The thermal contrast for the j$^{th}$ plume gas for the i$^{th}$ pixel was determined by specifying the column density, $g_{jP}(i)$ and plume temperature, $T_{P(i)}$. Column densities for the plumes were designated in units of ppmm.

In a second set of experiments, different synthetic ammonia gas plumes were added to the pre-plume, atmospherically compensated TIR data, with each plume having a constant column density and temperature. However, due to pixel temperature differences in the pre-plume, atmospherically compensated data, the thermal contrast varied as a function of pixel position. Eleven synthetic ammonia plumes were generated, with the column density for each plume set at 2.5, 3, 4, 5, 6, 7, 8, 9, 10, 15 and 20 ppmm, and the plume temperatures fixed at 60° C. For a column density of 2.5 ppmm and a plume temperature of 60° C., the mean thermal contrast of the plume is 1146 ppmm-μf, which is near the estimated minimum detectable quantity of 700 ppmm-μf for ammonia. See S. J. Young.

Figure 6:
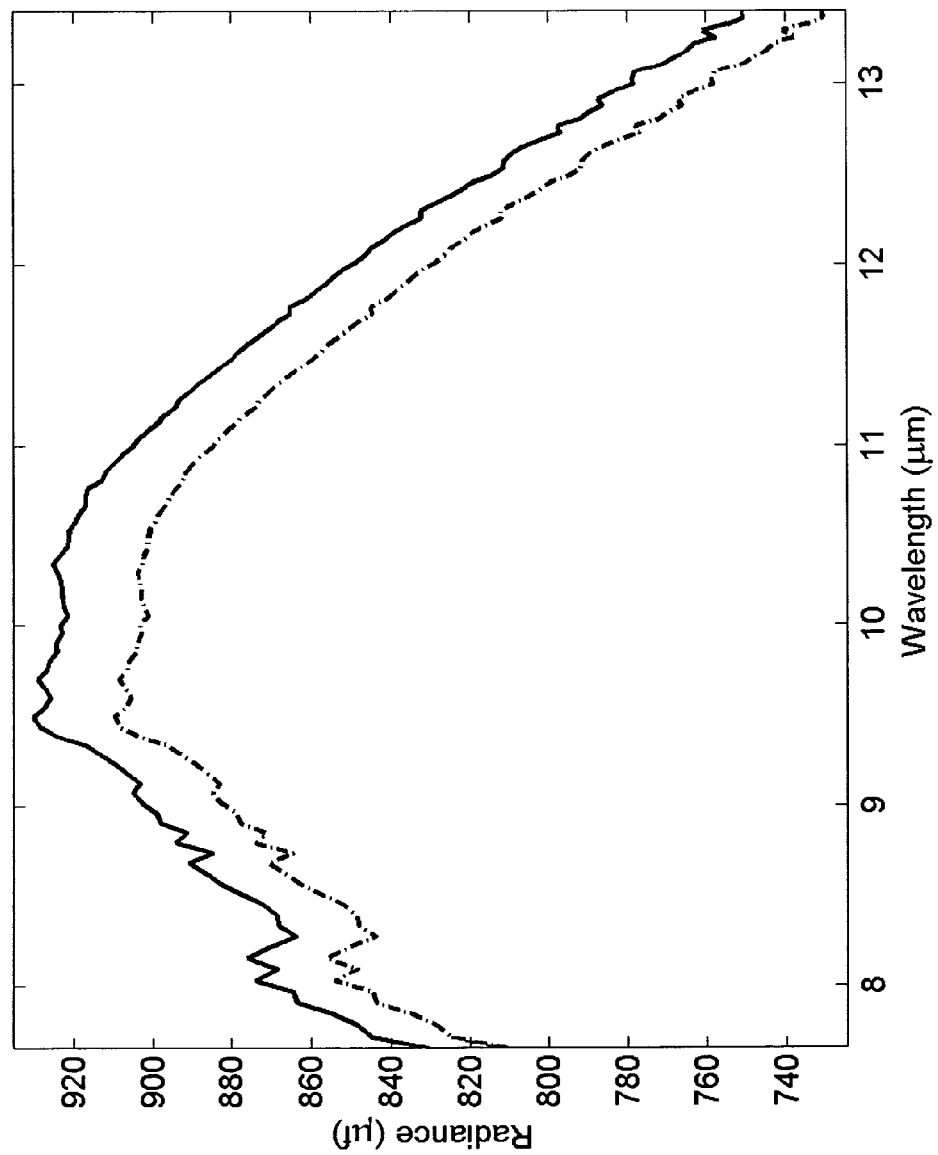
FIG. 6 shows an atmospherically compensated pixel spectrum before (-.) and after (-) the addition of ammonia plume with column density of 2.5 ppmm and thermal contrast of 1596 ppmm-µf. The post-plume spectrum is offset by 20 µf.

In FIG. 6 is shown a comparison of the atmospherically compensated spectrum for a representative pixel before and after the addition of an ammonia plume at a column density of 2.5 ppmm and a thermal contrast of 1596 ppmm-μf. The post-plume spectrum is offset by 20 μf for visual clarity. The characteristic spectral features of ammonia are barely discernable in the post-plume spectrum.

For each of the eleven post-plume, atmospherically compensated TIR data sets, $X_{c,P}$, the multi-step analysis shown in FIG. 3 was performed at step 60.

At step 61, SVD was applied to the atmospherically compensated, post-plume TIR data, $X_{c,P}$, and used to calculate the m by n left singular matrix, U, the n by n right singular matrix, V, and the n by n singular value matrix, $\Sigma$, which optimally described the variance in the scene. At step 62, the number of retained components, p, was determined by comparing images constructed from the left singular matrix, U, to the known spatial distribution of the plume. All the components required to model the plume were retained. While in this example the spatial distribution of the synthetic plume was known a priori, in the absence of such knowledge one could use a plume detection algorithm such as spectral matched filters to delineate the spatial boundaries of the plume and select the appropriate number of retained components.

At step 63, Varimax rotation was applied to the m by p left singular matrix, $U_p$, corresponding to the p retained columns of U. A p by p rotation matrix, R, was calculated which maximized the spatial simplicity of the rotated $U_p$ matrix. At step 64, the inverse rotation was applied to $\Sigma_p V_p^T$. For the TIR data used herein, Varimax rotation was consistently successful in deriving abundance estimates which were representative of the major components within the remote scene, namely vegetation, the parking lot, the building and the synthetic plume. Varimax rotation also consistently derived accurate endmember estimates for non-plume components in the scene. Employing Varimax rotation, the synthetic plume was localized to a single component.

At steps 65 and 66, MCR was applied to the Varimax-rotated atmospherically compensated, post-plume TIR data, $X_{c,P} = \tilde{C}\tilde{S} + E$. A preprocessing step was performed such that rows of the Varimax endmember matrix, $\tilde{S}$, taking on negative values were multiplied by $-1$ to ensure that the pre-processed Varimax endmembers were all non-negative. The corresponding columns of the Varimax abundance matrix, $\tilde{C}$, were also multiplied by $-1$. The endmembers for the (p$-1$) non-plume components were initialized using the corresponding rows of the pre-processed Varimax endmember matrix, while the endmember profile for the plume component was initialized using randomly selected, uniformly distributed values ranging between zero and one. For the plume component, an equality constraint was applied to the pre-processed Varimax plume abundance estimate. A non-negativity constraint was applied to the endmembers for all p components. Steps 65 and 66 were iterated until convergence. 1000 MCR iterations were performed. All calculations and programs were implemented in MATLAB 6.5 (The Mathworks, Inc., Natick, Mass.).

Figure 7B:
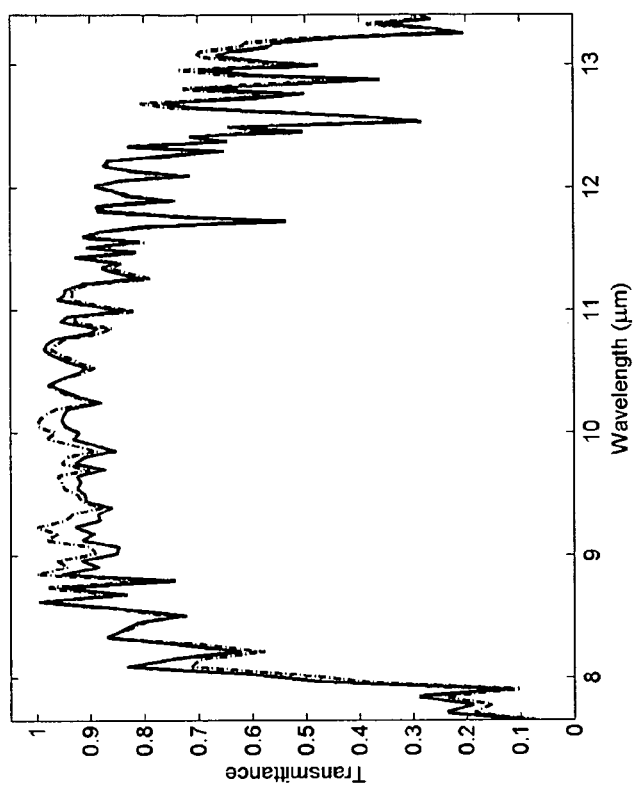
FIGS. 7A-B show MCR (-) and Inscene Atmospheric Compensation (ISAC) (-.) estimates of atmospheric upwelling (FIG. 7A), and atmospheric transmittance (FIG. 7B).
Figure 7A:
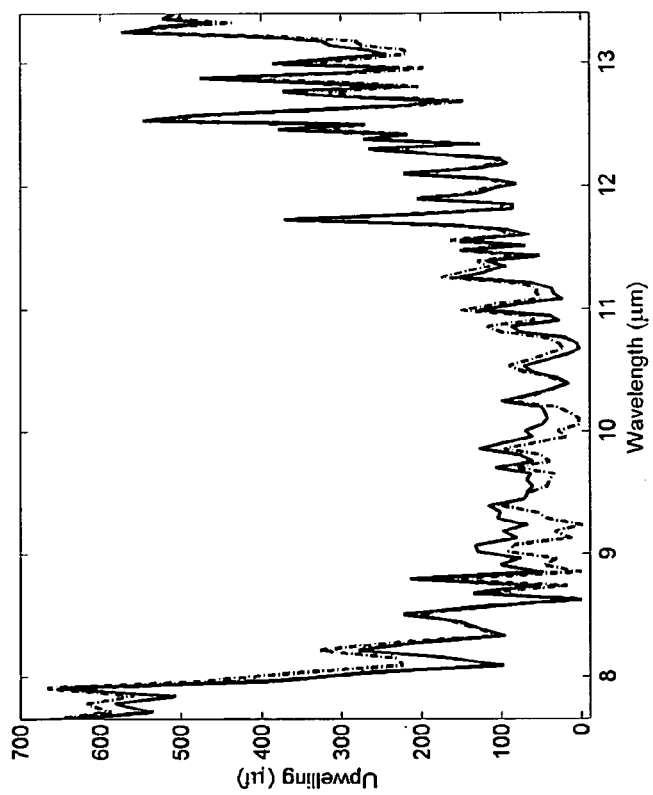

In FIG. 7(a) is shown the MCR estimate of the atmospheric upwelling, obtained using the uncompensated TIR data, and a comparison of this to the upwelling obtained using the ISAC algorithm. A close correspondence is noted between the MCR and ISAC estimates of the upwelling at higher wavelengths, particularly above 11.5 μm. This is despite the fact that the MCR upwelling estimate was obtained utilizing only a small part of the overall image data. Discernable discrepancies in the upwelling estimates, however, are evident below 11 μm. A significant divergence is seen between 9 and 101m, a region of atmospheric ozone absorption. In FIG. 7(b) is shown a plot of the MCR and ISAC estimates of the atmospheric transmittance. There is a close correspondence in the shapes of the two transmittance estimates, with absolute transmittance value differences ranging between 0.0007 and 0.12. The similarity between the MCR and ISAC estimates of the atmospheric upwelling and transmittance is good, indicating that MCR is capable of providing atmospheric compensation results consistent with the de facto standard. In particular, MCR can generate reasonable atmospheric upwelling and transmittance estimates utilizing only a small 28 pixel by 33 pixel image subregion of the overall 128 pixel by 1000 pixel image. MCR is capable of generating local atmospheric models because it uses all the pixels within a given scene in deriving its atmospheric upwelling and transmittance estimates.

Figure 8B:
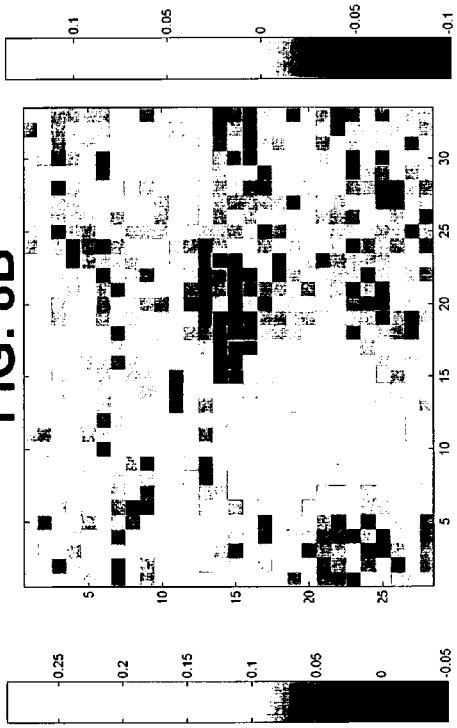
FIGS. 8A-C show Varimax abundance estimates at ammonia column density of 2.5 ppmm for building (FIG. 8A), vegetation (FIG. 8B), and plume (FIG. 8C).
Figure 8A:
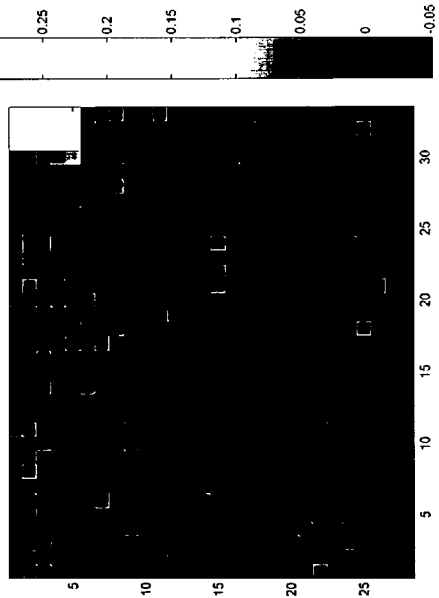
Figure 8C:
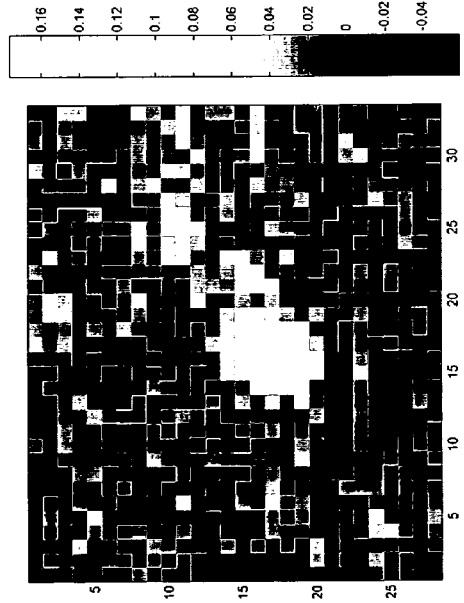
Figure 9:
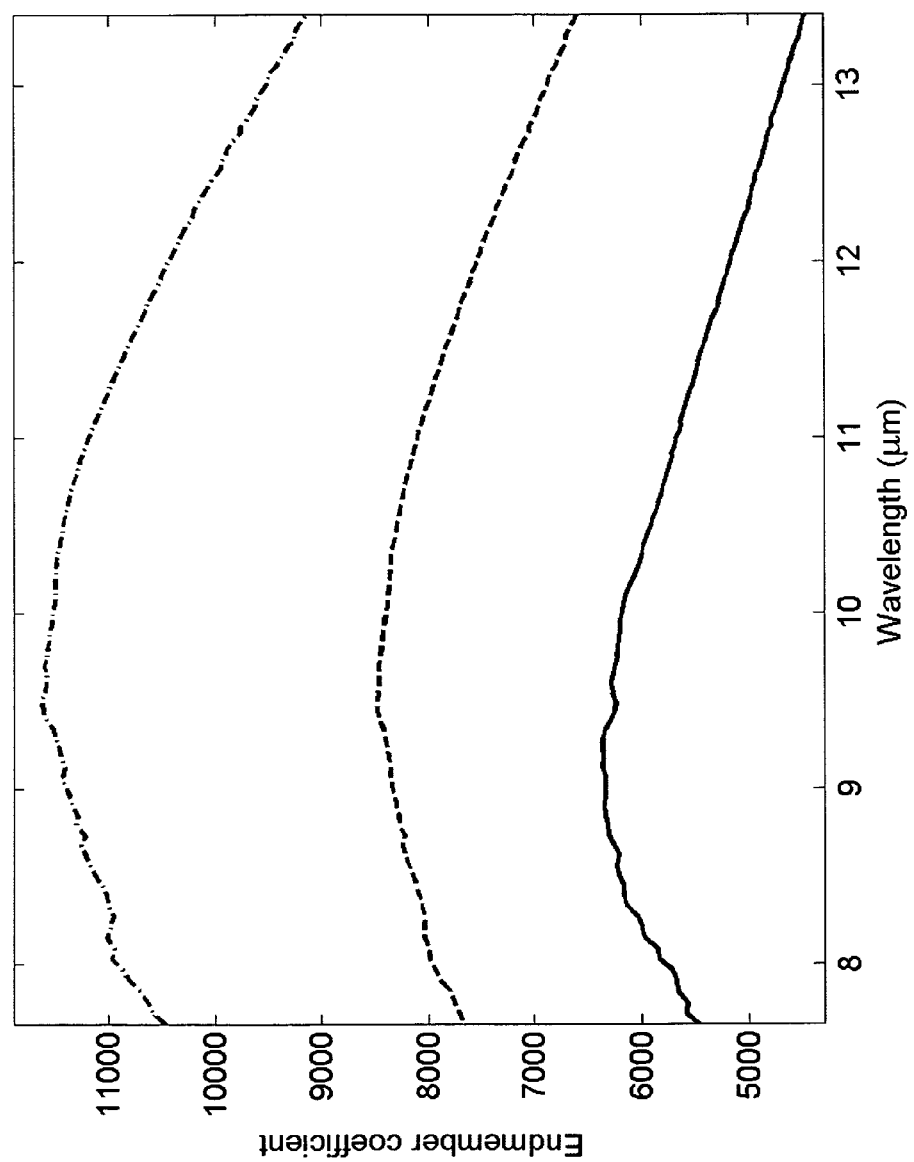
FIG. 9 shows Varimax endmember estimates for building (-), vegetation (-.), and plume (--) at ammonia column density of 2.5 ppmm.

Following MCR-based atmospheric compensation of the TIR data, synthetic gas plumes were added to the data. SVD and Varimax rotation were then applied to the post-plume, atmospherically compensated data. In FIGS. 8 and 9 are shown the Varimax abundances and endmembers which best represent the building, vegetation, and plume obtained at an ammonia column density of 2.5 ppmm. The abundance image in FIG. 8(a) describes the building in the upper right hand corner of the analyzed region, the abundance image in FIG. 8(b) describes the tree in the lower left hand quadrant of the analyzed region, while the abundance image in FIG. 8(c) captures the spatial distribution of the plume. The corresponding endmembers obtained by Varimax rotation, shown in FIG. 9, are very similar spectrally. The Varimax endmembers for the building and vegetation are consistent with expectations for graybody objects, having smooth spectral features. The Varimax endmember estimate for the plume, however, does not match the spectral absorption coefficients for ammonia. This inconsistency is attributable to the fact that Varimax rotation using the spatial simplicity criterion cannot unmix the plume from the underlying surface pixels, resulting in a graybody-like endmember profile characteristic of the surface.

MCR was then applied to the Varimax-rotated, atmospherically compensated, post-plume TIR data. Table 1 summarizes the results for the second set of experiments, where synthetic ammonia gas plumes were added to the atmospherically compensated TIR data. The table lists the true mean thermal contrast for the synthetic ammonia plume, the correlation coefficient between the MCR-estimated relative thermal contrast and the true thermal contrast for the synthetic ammonia plume, the correlation coefficient between the MCR-estimated relative spectral absorption coefficients and the true resampled spectral absorption coefficients for ammonia, and the number of retained components in the MCR model for each of the eleven ammonia column densities. It is apparent that the thermal contrast correlation and the spectral absorption coefficient correlation increase as the ammonia plume column density and the mean thermal contrast increases. This is consistent with expectation that MCR achieves more accurate estimates of the relative thermal contrast and spectral absorption coefficients as the column density of the ammonia plume increases.

TABLE 1

Summary of second set of experiments where synthetic ammonia plumes were added to the atmospherically compensated TIR data.

| Column Density (ppmm) | Mean thermal contrast (ppmm-µf) | Thermal contrast correlation | Spectral absorption coefficient correlation | Number of retained components |
|---|---|---|---|---|
| 2.5 | 1146 | 0.701 | 0.679 | 40 |
| 3 | 1375 | 0.767 | 0.719 | 35 |
| 4 | 1833 | 0.842 | 0.803 | 27 |
| 5 | 2292 | 0.867 | 0.892 | 23 |
| 6 | 2750 | 0.884 | 0.865 | 19 |
| 7 | 3208 | 0.941 | 0.930 | 19 |
| 8 | 3667 | 0.954 | 0.928 | 18 |
| 9 | 4125 | 0.965 | 0.955 | 18 |
| 10 | 4584 | 0.970 | 0.965 | 18 |
| 15 | 6875 | 0.975 | 0.980 | 15 |
| 20 | 9167 | 0.977 | 0.982 | 11 |

In FIGS. 10(a), (b) and (c) are shown plots of the MCR-estimated, normalized spectral absorption coefficients at ammonia column densities of 2.5, 5 and 10 ppmm and comparisons of these estimates to the true resampled, normalized spectral absorption coefficients for ammonia. Here, normalization refers to scaling a given vector to unit length. As shown in FIG. 10(a), at a column density of 2.5 ppmm, the MCR-estimated spectral absorption coefficients accurately reflect the two dominant spectral peaks at 10.34 and 10.76 µm which are characteristic of ammonia. However, there are numerous inconsistencies between the MCR-estimated spectral absorption coefficients and the true, normalized spectral absorption coefficients, most notably below 8.5 µm and above 12.5 µm. MCR's inability to model ammonia's minor spectral peaks can likely be attributed to the fact that the plume signal intensity in these spectral regions are at or below the noise level for the SEBASS sensor, estimated to be between 0.4 to 0.9 µf. See B. R. Johnson. As shown in FIG. 10(b), at a column density of 5 ppmm, there is greater correspondence between the MCR-estimated spectral absorption coefficients and the true resampled, normalized spectral absorption coefficients for ammonia. At a column density of 5 ppmm, MCR correctly models the two dominant ammonia spectral peaks at 10.34 and 10.76 µm, along with some minor ammonia spectral peaks between 11 and 12 µm and 9 and 10 µm. There are, however, significant discrepancies between the MCR-estimated spectral absorption coefficients and the true resampled, normalized spectral absorption coefficients for ammonia below 9 µm. As indicated in FIG. 10(c), at a column density of 10 ppmm there is a very close correspondence between the MCR-estimated and true resampled, normalized spectral absorption coefficients, even for many of the minor spectral peaks which are characteristic of ammonia. MCR converged to an answer that is strongly correlated with the true spectral absorption coefficients even though the endmember profile for the plume component was initialized using random numbers. Significant discrepancies are apparent below 8.6 µm and above 12.8 µm, which are likely attributable to residual atmospheric effects in the atmospherically compensated TIR data.

In FIGS. 11(a), (b), (c) and (d) are shown the true, normalized thermal contrast image for the ammonia plume and the Varimax-estimated, normalized thermal contrast images corresponding to column densities of 2.5, 5 and 10 ppmm, respectively. Normalizing each of the true thermal contrast images at column densities of 2.5, 5 and 10 ppmm resulted in identical images, and thus only a single true, normalized thermal contrast image is displayed. There is a close correspondence between the true, normalized thermal contrast image in FIG. 11(a) and the MCR-estimated, normalized thermal contrast images at column densities of 2.5, 5 and 10 ppmm, depicted in FIGS. 11(b), (c) and (d). In comparing the figures, it is apparent the correlation between the true, normalized thermal contrast image and the MCR-estimated, normalized thermal contrast images increases as the column density of ammonia increases.

The present invention has been described as a method to analyze remotely sensed spectral data using multivariate curve resolution. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method to analyze remotely sensed spectral data, comprising:
   (a) acquiring a remotely sensed spectral data set, X;
   (b) modeling the data set according to $X = C_{true}S_{true}T + 1a^T + E_{instr}$, where $C_{true}$ is a matrix of true abundances for components contained within a remote scene, $S_{true}$ is a corresponding matrix of true spectral endmembers for the components, T is a matrix of atmospheric transmittance values, 1 is a vector of ones, $a^T$ is a vector representing an additive, atmospheric component, and $E_{instr}$ is a matrix describing instrument noise;
   (c) calculating the atmospheric transmittance matrix T and additive atmospheric component $a^T$ to provide an atmospherically compensated data set according to $X_c = (X - 1a^T)T^{-1} = C_{true}S_{true} + E_{instr}$; and
   (d) obtaining a multivariate curve resolution (MCR) estimate of $C_{true}$ and $S_{true}$, subject to constraints.

2. The method of claim 1, wherein the data set X comprises solar-reflective spectral data.

3. The method of claim 1, wherein the data set X comprises midwave infrared spectral data.

4. The method of claim 1, wherein step (d) comprises Principal Component Analysis (PCA) factorization of the atmospherically compensated data set $X_c$, rotation of the PCA factors to provide a rotated abundance matrix $\tilde{C}$ and a rotated endmember matrix $\tilde{S}$, and MCR of the rotated abundance and endmember matrices to obtain the estimates of $C_{true}$ and $S_{true}$.

5. The method of claim 4, wherein the PCA factorization comprises nonlinear iterative partial least squares, eigenanalysis, or singular value decomposition.

6. The method of claim 4, wherein the rotation of the PCA factors comprises Quartimax or Varimax rotation.

7. A method to analyze remotely sensed spectral data, comprising:

(a) acquiring a remotely sensed thermal infrared data set, X;

(b) modeling the data set according to $$X = GKT + BFT + 1I_u^T + E_{instr} = [G \ B \ 1] \begin{bmatrix} KT \\ FT \\ I_u^T \end{bmatrix} + E_{instr},$$

where G is a matrix of thermal contrast coefficients for plume gases, K is a matrix of spectral absorption coefficients for the plume gases, B is a matrix of amplitude coefficients for solids, F is a matrix of spectral coefficients for the solids, T is a diagonal matrix of atmospheric transmittance values, 1 is a vector of ones, and $I_u^T$ is a vector containing atmospheric upwelling terms, and $E_{instr}$ is a matrix describing instrumental noise;

(c) obtaining a multivariate curve resolution (MCR) estimate of the atmospheric upwelling $I_u^T$, subject to constraints;

(d) calculating the atmospheric transmittance matrix T to provide an atmospherically compensated data set according to $$X_c = (X - 1I_u^T)T^{-1} =$$
$$GK + BF + E_{instr} = [G \ B] \begin{bmatrix} K \\ F \end{bmatrix} + E_{instr} = C_{true}S_{true} + E_{instr};$$

and (e) obtaining an MCR estimate of G, K, B, and F, subject to constraints.

8. The method of claim 7, wherein the constraint in step (c) comprises a constant abundance constraint.

9. The method of claim 7, wherein step (d) comprises estimating the atmospheric transmittance matrix T according to $\bar{\epsilon}_s(\lambda)\tau(\lambda)=(\bar{x}(\lambda)-I_u(\lambda))/B_s(\lambda,\bar{T})$, where $\bar{\epsilon}_s(\lambda)$ is the mean surface emissivity over all the pixels at wavelength $\lambda$, $\bar{T}$ is the mean surface temperature over all the pixels, $B_s(\lambda, \bar{T})$ is the Planck blackbody radiance function evaluated at wavelength $\lambda$ and the mean surface temperature $\bar{T}$, $\tau(\lambda)$ is the atmospheric transmittance at wavelength $\lambda$, and $I_u(\lambda)$ is the atmospheric upwelling at wavelength $\lambda$.

10. The method of claim 7, wherein step (e) comprises Principal Component Analysis (PCA) factorization of the atmospherically compensated data set $X_c$, rotation of the PCA factors to provide a rotated abundance matrix $\tilde{C}$ and a rotated endmember matrix $\tilde{S}$, and MCR of the rotated abundance and endmember matrices to obtain the estimates of G, K, B, and F.

11. The method of claim 10, wherein the PCA factorization comprises nonlinear iterative partial least squares, eigenanalysis, or singular value decomposition.

12. The method of claim 10, wherein the rotation of the PCA factors comprises Quartimax or Varimax rotation.

* * * * *

UNITED STATES PATENT AND TRADEMARK OFFICE
CERTIFICATE OF CORRECTION

PATENT NO. : 7,491,944 B1  Page 1 of 1
APPLICATION NO. : 11/410445
DATED : February 17, 2009
INVENTOR(S) : Christopher L. Stork, Mark H. Van Benthem and Michael R. Keenan It is certified that error appears in the above-identified patent and that said Letters Patent is hereby corrected as shown below:

Title Pg, Item (75) Inventors: should read as follows:
--(75) Inventors: Christopher L. Stork, Albuquerque, NM (US)
Mark H. Van Benthem, Middletown, DE (US)
Michael R. Keenan, Wolcott, NY (US) --

Signed and Sealed this

Second Day of June, 2009

JOHN DOLL
*Acting Director of the United States Patent and Trademark Office*